United States Patent [19]

Budai et al.

[11] Patent Number: 4,511,737
[45] Date of Patent: Apr. 16, 1985

[54] BICYCLO(2.2.1)HEPTANE OXIMES

[75] Inventors: Zoltán Budai; Attila Kis-Tamás; Tibor Mezei; Aranka Lay; Zoltán Vigh; Ágnes Sokorai, all of Budapest, Hungary

[73] Assignee: EGYT Gyógyszervegyészeti Gyár, Budapest, Hungary

[21] Appl. No.: 551,941

[22] Filed: Nov. 15, 1983

Related U.S. Application Data

[62] Division of Ser. No. 322,675, Nov. 18, 1981, Pat. No. 4,425,158.

[30] Foreign Application Priority Data

Nov. 21, 1980 [HU] Hungary ............................... 2774/80

[51] Int. Cl.³ ........................................... C07C 131/02
[52] U.S. Cl. .................................................... 564/257
[58] Field of Search .......................... 564/257; 71/121

[56] References Cited

U.S. PATENT DOCUMENTS 4,425,158  1/1984  Budai et al. ............................ 71/121

Primary Examiner—Natalie Trousof
Assistant Examiner—L. Hendriksen
Attorney, Agent, or Firm—Keil & Weinkauf

[57] ABSTRACT

The invention relates to new bicyclo(2.2.1)heptane derivatives of the general formula I

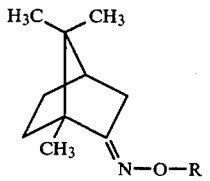

/I/ wherein

R represents a $C_{1-12}$ alkyl group optionally substituted by a lower alkoxy group, a $C_{2-4}$ alkenyl group or a phenyl-(lower alkyl) group optionally substituted on (I), phenyl ring by one or more lower alkoxy groups or halogen atoms.

The invention relates further to plant growth regulating compositions comprising as active agent 0.001 to 95% by weight of a racemic and/or optically active compound of the general formula I, wherein R has the above defined meanings, along with a conventional organic or inorganic, solid and/or liquid carrier and/or filler and/or diluent and/or surfactant.

The invention encompasses also the preparation of the compounds of the general formula (I) which comprises reacting a racemic or optically active compound of the general formula (II)

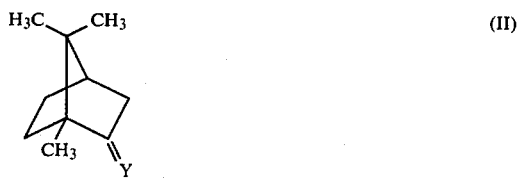

(II)

wherein

Y is an oxygen or sulfur atom or an oxim group, with a compound of the general formula (III)

R—X wherein

R is as defined above, and

X represents a leaving group, preferably a halogen atom, a sulfonyloxy or an aminooxy group, with the proviso that when using a compound of the general formula (II), in which Y is an oxim group, X is other than aminooxy group, in the presence of a basic condensing agent, and optionally resolving the racemic compound of the general formula (I) obtained into its optically active antipodes.

3 Claims, No Drawings

BICYCLO(2.2.1)HEPTANE OXIMES

This is a division of application Ser. No. 322,675, filed Nov. 18, 1981, now U.S. Pat. No. 4,425,158.

The invention relates to new bicyclo(2.2.1)heptane derivatives and to plant growth regulating compositions containing same. The invention encompasses also the preparation of the active agents.

According to a feature of the present invention there are provided new bicyclo(2.2.1)heptane derivatives corresponding to the general formula (I)

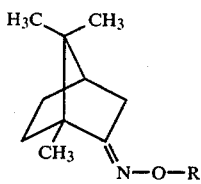

wherein

R represents a $C_{1-12}$ alkyl group optionally substituted by a lower alkoxy group, a $C_{2-4}$ alkenyl group or a phenyl-(lower alkyl) group optionally substituted on the phenyl ring by one or more lower alkoxy groups or halogen atoms.

The term "$C_{1-12}$ alkyl group" used in the specification and claims relates to straight-chained or branched saturated aliphatic hydrocarbyl groups containing 1 to 12 carbon atoms, such as methyl, ethyl, n-propyl, isopropyl, n-butyl, n-hexyl, n-dodecyl, etc. These alkyl groups can optionally carry a lower alkoxy substituent. The term "lower alkoxy group" relates to straight-chained or branched alkoxy groups containing 1 to 4 carbon atoms e.g. methoxy, ethoxy, isopropoxy, etc. As alkoxyalkyl group the methoxymethyl, ethoxymethyl and ethoxyethyl groups are mentioned. The term "$C_{2-4}$ alkenyl group" refers to straight-chained or branched alkenyl groups containing 2 to 4 carbon atoms e.g. vinyl, allyl, 2-propenyl, etc. The term "phenyl-(lower alkyl) group" relates to straight-chained or branched alkyl groups containing 1 to 4 carbon atoms substituted by one or two phenyl groups e.g. benzyl, β-phenylethyl, β,β-diphenylethyl, etc. The phenyl-(lower alkyl) groups may carry one or more halogen and/or lower alkoxy substituents on the phenyl ring e.g. p-chlorobenzyl, etc. The term "halogen atom" may stand for all the four halogen atoms, such as fluorine, chlorine, iodine and bromine.

The compounds of the general formula (I) contain an asymmetric carbon atom, consequently they exist in the form of a racemic mixture or optically active antipodes. The invention embraces the racemic and optically active forms of the compounds of the general formula (I), too. The term "a compound of the general formula (I)" used in the specification relates to the racemic compounds of the general formula (I) and also to the optically active antipodes.

Preferred representatives of the new compounds having the general formula (I) are those wherein R stands for an alkyl group containing 1 to 4 or 10 to 14 carbon atoms, or an allyl or a benzyl group.

Of the new compounds of the general formula (I) the following are particularly preferred:

(±)-2-(n-propoxyimino)-1,7,7-trimethyl-bicyclo(2.2.1-)heptane, (−)-2-(n-propoxyimino)-1,7,7-trimethyl-bicyclo(2.2.1-)heptane, (±)-2-(dodecyloxyimino)-1,7,7-trimethyl-bicyclo(2.2.1-)heptane, (±)-2-(allyloxyimino)-1,7,7-trimethyl-bicyclo(2.2.1-)heptane, (−)-2-(allyloxyimino)-1,7,7-trimethyl-bicyclo(2.2.1-)heptane, (±)-2-(benzyloxyimino)-1,7,7-trimethyl-bicyclo(2.2.1-)heptane.

According to a further feature of the invention there are provided plant growth regulating compositions comprising as active agent 0.001 to 95% by weight of a racemic and/or optically active compound of the general formula (I), wherein R has the same meanings as defined above, along with a conventional organic or inorganic, solid and/or liquid carrier and/or filler and/or diluent and/or surfactant.

The compositions according to the invention contain 0.001 to 95% by weight of active agent. The invention embraces the concentrates of high active agent content as well as the diluted compositions ready for use.

The racemic or optically active compounds of the general formula (I) or the mixtures thereof can be converted into compositions, such as emulsifiable concentrates EC, foils such as sowing-seed foils, granulates preferably microgranulates, etc. in a known way. These compositions contain the racemic or optically active new compounds of the general formula (I) or the mixtures thereof in the following: "active agent" in combination with solid or liquid inert carriers or diluents, solvents and other auxiliary agents.

Of the auxiliary agents e.g. surfactants such as wetting, emulsifying and dispersing agents, anticaking agents, adhesives, lubricants, sticking aids, dyestuffs, corrosion inhibitors, suspending agents, substances increasing the resistance against rain, penetration aids, etc. are to be mentioned.

As solid carriers or diluents e.g. inert mineral substances, such as aluminium silicate, talc, ignited magnesia, silica, tricalcium phosphate, cork meal, coke powder, clays, kaoline, pearlite, bentonite, montmorillonite, diatomaceous earth, pyrophillite, dolomite, gypsum, calcium phosphate, calcium carbonate, mica, colloidal silicon dioxide, Fuller's earth, Hewitt's earth, china clay, etc. can be used.

As liquid carriers or diluents e.g. aqueous, organic and/or aqueous-organic solvents, such as water, ketones e.g. acetophenone, cyclohexanone, isophoron, etc., aromatic hydrocarbons e.g. benzene, toluene, xylene, etc., alkylnaphthalenes, tetrahydronaphthalene, chlorinated hydrocarbons e.g. chlorobenzenes, dichloroethylene, trichloroethylene, tetrachloroethane, etc., alcohols e.g. methanol, ethanol, isopropanol, butanol, propylene glycol, diacetone alcohol, etc., kerosine, mineral, animal and vegetable oils, aliphatic mineral oil fractions, petrol distillates with high aromatic contents e.g. naphta and distilled tar oil, polar organic solvents e.g. dimethyl sulfoxide and dimethyl formamide, and mixtures thereof can be used.

The wetting, dispersing and emulsifying surfactants can be ionic or non-ionic in type.

As non-ionic surfactants e.g. condensates of ethylene oxide with $C_{10-20}$ fatty alcohols such as oleyl alcohol, cetyl alcohol, octadecyl alcohol, etc., alkylphenols such as octylphenol, octylcresol, etc., amines such as oleylamine, mercaptans such as dodecylmercaptan or carboxylic acids, partial esters of higher fatty acids and hexitol anhydrides, condensation products of these partial esters and ethylene oxide, lecithins, fatty acid esters of polyalcohols, etc. can be applied.

The ionic surfactants can be cationic or anionic compounds.

Of the cationic surfactants e.g. the quaternary ammonium compounds such as cetyl-trimethyl-ammonium bromide, cetylpyridinium bromide, etc. are to be mentioned.

Examples of the anionic surfactants are soaps, salts of aliphatic monoesters of sulfuric acid such as sodium laurylsulfate, sodium salt of dodecanol monosulfate, salts of sulfonated aromatic compounds such as sodium dodecyl benzenesulfonate, sodium-, calcium- or ammonium ligninsulfonate, butylnaphthalenesulfonate, mixtures of the sodium salts of di- and triisopropyl-naphthalenesulfonic acid, sodium salts of petroleumsulfonic acids, potassium or triethanolamine salts of oleic acid or abietic acid, etc.

As suspending agents, e.g. hydrophilic colloids such as polyvinyl pyrrolidone, sodium carboxymethyl cellulose, etc., furthermore gums of vegetable origin such as tragacanth gum, etc. can be applied.

Examples of sticking aids are lubricants such as calcium or magnesium stearate, adhesives such as polyvinyl alcohol, cellulose derivatives and other colloidal substances such as cassine, mineral oils, etc.

Of the dispersing agents e.g. methyl cellulose, ligninsulfonates, alkylnaphthalenesulfonates, etc. are to be mentioned.

As distribution aids, sticking aids, agents for increasing rain resistance or penetration aids e.g. fatty acids, resins, glue, caseine and alginates can be applied.

Utilizing the carriers, diluents and auxiliary agents mentioned above, the active agent according to the invention can be converted into various solid, liquid or gaseous agricultural or horticultural compositions.

Examples of the solid compositions are grains and granulates, preferably microgranulates, pastes, granulated, dressed or—preferably—coated seeds, agricultural primarily horticultural sowing-seed foils, etc.

Of the liquid compositions the following are to be mentioned: solutions, such as directly sprayable solutions e.g. aqueous solutions, solutions formed with organic solvents or oils, miscible oils, etc., dispersions, suspensions, primarily aqueous suspensions, aqueous or oily emulsions, invert emulsions, etc.

The granular compositions can be prepared e.g. by dissolving the plant growth regulating agent of the invention in a solvent, and applying the solution onto a granular carrier e.g. a porous granular substance, such as pumice stone or attaclay, a non-porous granular mineral substance, such as sand or loam, or a granular organic substance, such as black soil or cut tobacco stalk, in the presence of a binding agent, and, if desired, drying the resulting granular substance. According to another method, granular compositions are prepared by admixing the plant growth regulating agent with a powdered mineral substance, a lubricant and a binding agent, compressing the mixture, crushing the compressed substance, and separating the fraction with the required grain size by sieving. A preferred method of preparing granular compositions is dry or wet granulation, the latter being performed either by wet compression or by buildup technique.

A particularly preferred form of the compositions is the sowing-seed foil. As well known, in order to facilitate the sowing of seeds and to ensure uniform distances between the individual seeds and rows, manual sowing or planting is increasingly replaced in the agriculture, primarily in the horticulture, by incorporating the seeds into a water-soluble foil, and placing the resulting foil bands, which contain optionally more than one row of seeds, into the soil. The foil can be made of any water-soluble substance inert towards the seeds, such as polyvinyl alcohol; the only requirement is that the foil does not damage the seeds and disintegrates or dissolves in the soil upon the effect of moisture. The sowing-seed foil according to the invention may contain the new active agent incorporated into the foil material, or seeds pre-treated with the new active agent can be incorporated into the foil. It is a particular advantage of the sowing-seed foils that the new active agent increases primarily the germination ability of the seeds in the foil and then promotes primarily the growth of the plants to be cultivated, also providing an appropriate protection against insect pests during the initial development of the plants.

Dispersions, suspensions or emulsions can be prepared by dissolving or suspending the active agent according to the invention in a solvent which contains optionally one or more wetting, dispersing, suspending and/or emulsifying agents, and admixing the resulting mixture with water, also containing optionally one or more wetting, dispersing, suspending and/or emulsifying agents.

Miscible oils can be prepared by dissolving or finely dispersing the active agent of the general formula (I) in an appropriate solvent, preferably in a solvent slightly miscible with water, in the presence of an emulsifying agent.

Solutions for direct spraying are prepared by dissolving the active agent according to the invention in a solvent with medium to high boiling point. It is preferred to apply a solvent boiling above 100° C.

Invert emulsions can be prepared by emulsifying an emulsion of the active agent according to the invention in water directly in the spraying apparatus either before or during spraying.

Emulsifiable concentrates, pastes or wettable spray powders can be applied particularly preferably to prepare aqueous formulations ready for use. These concentrates are diluted prior to use with water to the required concentration. The concentrates should be stable for a prolonged period of storage, and, after dilution with water, they should form aqueous compositions which remain homogeneous for a time sufficient to apply them with a conventional spraying apparatus. The concentrates generally contain 10 to 85% by weight, preferably 25 to 60% by weight, of active agent. The diluted aqueous compositions spray liquids ready for use contain preferably 0.001 to 3.00% by weight of active agent, however, for specific applications, compositions with higher or lower active agent content can also be prepared.

Depending on the method of preparation and application, the active agent content of the compositions required to have the desired effect may vary over a broad range. The compositions contain generally 0.01 to 95% by weight of active agent. When the composition is to be applied according to the "ultra-low volume" ULV technique, the active agent according to the invention can be admixed with extremely small amounts of additives to form compositions containing preferably 90 to 95% by weight of active agent. These compositions are applied to the desired places with an apparatus producing extremely fine sprays, preferably from an aeroplane. Diluted compositions contain generally 0.01 to 20% by weight of active agent, whereas the active agent content of concentrates may vary generally between 20 and 95% by weight.

The emulsifiable concentrates contain generally 5 to 70% by weight, preferably 10 to 50% by weight, of active agent. The active agent content of powdery compositions may be generally 0.5 to 10% by weight, preferably 1 to 5% by weight.

The compositions according to the invention can be applied as sprays, powders sprays, coating agents e.g. for seed coating, sowing-seed foils, soil watering compositions, dip-in baths, etc. The type of composition to be applied depends on the requirements of the field of application.

The invention relates further to an agricultural process, in which the plants, seeds and/or the soil is (are) treated either directly or indirectly with a composition containing a racemic or optically active compound of the formula (I) or their mixture.

In this agricultural process the compositions according to the invention are applied onto or into the soil, onto the seeds or plants, or onto a pre-selected part of the plants.

Seeds can be treated e.g. by coating them with the active agent according to the invention, optionally along with a carrier, under stirring. The active agent of the invention can also be applied onto seeds along with wetting surfactants as defined above and optionally with a carrier. In this latter instance the mixture of the active agent, surfactant and carrier is wetted first with a small amount of water, and the seeds are admixed with the resulting suspension.

A specific method of seed treatment is seed coating according to the dragée-producing technique. This can be performed e.g. by placing the seeds into a dragépan, rotating the pan, and wetting the seeds with an aqueous solution of a binding agent e.g. sodium carboxymethyl cellulose. Thereafter the coating agent, a powdery mixture, is sprayed onto the surface of the wet seeds. The coating agent is administered until the required final weight or dimension of the coated seeds is reached.

The agricultural process according to the invention can also be performed so that the active agent is admixed with soil, sand or another powdered solid carrier listed above and optionally with a surfactant, and the resulting powder mixture is applied into the furrows during sowing.

The active agent can be applied onto the seeds prior to, simultaneously with, or after sowing, either according to the agricultural methods discussed above, or in the form of an aqueous spray containing the active agent optionally along with a surfactant and/or a powdered solid substance as defined above.

The agricultural treatment method of the invention can also be performed by applying the composition containing the active agent directly to the plant, to certain parts e.g. the leaves of the plants, or to the environment of the plants. The compositions can be applied to the desired place e.g. by spraying, dusting, etc. The compositions can also be applied into the soil, e.g. by watering, flooding or incorporation techniques. According to the latter, the seeds are sown into furrows pre-treated with the composition in question.

The compositions according to the invention can be used for regulating the growth of both monocotyledons and dicotyledons. Pre-sowing, pre-planting, pre-emergent and post-emergent treatment methods, furthermore incorporation into soil can equally be applied.

The term "pre-sowing" or pre-planting" means that the compositions according to the invention are applied onto the soil first, and sowing or planting is performed after this operation.

The term "pre-emergent treatment" means that the compositions according to the invention are applied onto the soil prior to plant emergence, e.g. by spraying the soil before the germinating plants break through the soil surface.

The term "post-emergent treatment" means that the compositions according to the invention are applied onto the area to be treated e.g. onto the plants or soil after the plants have emerged.

According to our experiences the compositions according to the invention are particularly useful in regulating the growth of corn, cereals, sunflower, alfalfa, sugar beet, rape, soybean, potato, rice, green pepper, tomato and vegetables.

The dosage of the active agent required to attain the desired effect depends on several factors, such as the optical activity of the active agent racemic, dextrorotatory, laevorotatory, the type and general state of the cultivated plant to be treated, the development stage of the cultivated plant seed, germinating seedling, 1 to 3 leaves' stage, etc., the type of other plants growing in the environment of the plant to be treated, the season, meteorological conditions, the method of applying the composition, pre-emergent, pre-sowing, pre-planting, post-emergent, incorporation into soil, etc., and on the actual form of the composition. Accordingly, the optimum dosage should always be determined empirically. The active agent is generally applied in a dosage of 0.1 to 25 kg/hectare, preferably 0.1 to 15 kg/hectare. The optimum dosage of seed dressing or germination promoting is about 5 to 500 g/100 kg of seeds. When plant growth promoting or crop yield increasing effect is desired, or soil treatment is performed, the optimum dosage varies between 0.1 and 15 kg/hectare.

The final concentration of the diluted compositions ready for use also depends on the field of application e.g. seed treatment, treatment of leaves, application onto soil, incorporation into soil, etc. Thus e.g. diluted compositions containing 0.5 to 10.000 ppm, preferably 1 to 1000 ppm, of active agent are applied for seed and leaf treatment, as well as to increase germination power, whereas pre-emergent and post-emergent treatments are performed with diluted compositions e.g. spray liquids generally containing 0.1 to 3.0% by weight, preferably 0.3 to 1.0% by weight, of active agent.

According to a further feature of the present invention there is provided a process for the preparation of the racemic or optically active compounds of the general formula (I), characterized by reacting a racemic or optically active compound of the general formula (II)

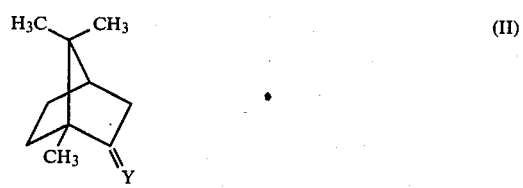

wherein

Y is an oxygen or sulfur atom or an oxim group, with a compound of the general formula (III)

R—X  (III)

wherein

R is as defined above, and

X represents a leaving group, preferably a halogen atom, a sulfonyloxy or an aminooxy group, with the proviso that when using a compound of the general formula (II), in which Y is an oxim group, X is other than aminooxy group, in the presence of a basic condensing agent, and optionally resolving the racemic compound of the general formula (I) obtained into the optically active antipodes.

In the compounds of the general formula (III) X may represent any leaving group usually applied for such reactions. X represents preferably a halogen atom or a sulfonyloxy group e.g. lower alkylsulfonyloxy group, such as methanesulfonyloxy group; or arylsulfonyloxy group, such as p-toluenesulfonyloxy, phenylsulfonyloxy or p-bromophenylsulfonyloxy group or an aminooxy group. When using starting substances of the general formula (II), wherein Y stands for an oxim group, compounds of the general formula (III), wherein X is other than aminooxy group, are used.

The reaction is carried out in the presence of a basic condensing agent. For this purpose alkali hydroxides e.g. sodium or potassium hydroxide, alkali hydrides e.g. sodium or potassium hydride, alkali amides e.g. sodium or potassium amide, alkali alcoholates e.g. sodium methylate, potassium ethylate, potassium tert.-butylate, etc., alkali metals e.g. sodium or potassium or organic bases e.g. triethylamine, picoline or pyridine are preferably used.

The reaction is preferably performed in an inert organic solvent. As reaction medium, aromatic hydrocarbons e.g. benzene, toluene, xylene, etc., acyclic or cyclic ethers e.g. diethyl ether, dibutyl ether, dioxane, tetrahydrofurane, etc., dipolar aprotic organic solvents e.g. dimethylformamide, dimethylacetamide, hexamethylphosphorous triamide, dimethylsulfoxide, etc. or alkanols e.g. methanol, ethanol, isopropanol, etc. or the mixtures thereof can be used.

The reaction is preferably carried out between 20° C. and the boiling point of the reaction mixture, preferably under heating, particularly at the boiling point of the reaction mixture.

The compounds of the general formula (I) thus-obtained are isolated from the reaction mixture by methods known per se, e.g. evaporation, fractionation, etc, and, if desired, purified by crystallization.

The compounds of the general formula (I) exist—as mentioned above—in the form of a racemic mixture or optically active antipodes. The optically active compounds of the general formula (I) can be prepared either by using optically active compounds of the general formula (II) as starting substance or by resolving the racemic compounds of the general formula (I) obtained into the optically active antipodes. Resolution is carried out by methods known per se.

The compounds of the general formulae (II) and (III) are known substances.

The plant growth regulating effect of the compounds having the general formula (I) are demonstrated by the results of the following tests:

A. Greenhouse Test

Plastic cultivation pots having 168 square centimeters were filled with washed river-sand, and the seeds of the plants to be tested, (corn, sunflower, pea, barley, wild rape and tomato, were sown 10 to 12 seeds into each pot. Pre-emergent treatment was carried out with a spray liquid simultaneously with sowing. Post-emergent treatment was performed with a spray liquid when plants became 2 to 4 leaves stage.

The individual tests were repeated four times, in "random" arrangement. A temperature of 18° to 24° C. in average was maintained during the test period. The plants were cultivated under natural lighting in a greenhouse.

The average of the green weights of the untreated control was taken as 100% and the averages of the individual treatments were compared to this value. A further averaging was also performed when relating the average weight of the monocotyledons and dicotyledons to that of the untreated control.

The following derivatives served as test compounds:

A=(±)-2-(dodecyloxyimino)-1,7,7-trimethyl-bicyclo(2.2.1)heptane.

B=(±)-2-(n-propyloxyimino)-1,7,7-trimethyl-bicyclo(2.2.1)heptane.

C=(−)-2-(allyloxyimino)-1,7,7-trimethyl-bicyclo(2.2.1)heptane.

D=(±)-2-(allyloxyimino)-1,7,7-trimethyl-bicyclo(2.2.1)heptane.

The results are given in Table I.

TABLE I

| Test compound | | Pre-emergence | | | Post-emergence | | |
|---|---|---|---|---|---|---|---|
| | | 0.5 | 2 | 5 | 0.5 | 2 | 5 |
| | | kg hectare | | | kg hectare | | |
| A | monocotyledonous | 111 | 132 | 130 | 116 | 101 | 100 |
| | dicotyledonous | 120 | 132 | 130 | 106 | 105 | 118 |
| B | monocotyledonous | 120 | 120 | 109 | 133 | 117 | 123 |
| | dicotyledonous | 112 | 130 | 118 | 120 | 113 | 115 |
| C | monocotyledonous | 102 | 109 | 145 | 128 | 100 | 109 |
| | dicotyledonous | 111 | 111 | 124 | 118 | 115 | 123 |
| D | monocotyledonous | 101 | 107 | 107 | 100 | 101 | 100 |
| | dicotyledonous | 131 | 119 | 105 | 115 | 113 | 102 |

An emulsifiable concentrate was prepared from the test compound A by the method of the Example 1. Thereafter it was diluted with water into spray liquid and used for the treatment of corn, sunflower and pea. The results are summarized in Table II:

TABLE II

| | Corn | | | Sunflower | | | Pea | | |
|---|---|---|---|---|---|---|---|---|---|
| | 0.5 | 2 | 5 | 0.5 | 2 | 5 | 0.5 | 2 | 5 |
| | kg/hectare | | | kg/hectare | | | kg/hectare | | |
| Pre-emergence | 120 | 165 | 155 | | 160 | | 180 | 180 | 220 |
| Post-emergence | 110 | 110 | 110 | | 110 | | 130 | 125 | 160 |

An emulsifiable concentrate was prepared from the test compound B by the method described in Example 1. Thereafter it was diluted with water into spray liquid and used for the treatment of corn, pea and tomato. The results are given in Table III:

TABLE III

|  | Corn | | | Pea | | | Tomato | | |
| --- | --- | --- | --- | --- | --- | --- | --- | --- | --- |
|  | 0.5 | 2 | 15 | 0.5 | 2 | 5 | 0.5 | 2 | 5 |
|  | kg/hectare | | | kg/hectare | | | kg/hectare | | |
| Pre-emergence | 140 | 140 | 120 | 140 | 200 | 190 | 95 | 120 | 102 |
| Post-emergence | 110 | 112 | 108 | 230 | 180 | 200 | 98 | 98 | 99 |

An emulsifiable concentrate was prepared from the test compound C by the method described in Example 1. Thereafter it was diluted with water into spray liquid and used for the treatment of corn, sunflower, pea and tomato. The results are summarized in Table IV:

TABLE IV

|  | Corn | | | Sunflower | | | Pea | | | Tomato | | |
| --- | --- | --- | --- | --- | --- | --- | --- | --- | --- | --- | --- | --- |
|  | 0.5 | 2 | 5 | 0.5 | 2 | 5 | 0.5 | 2 | 5 | 0.5 | 2 | 5 |
|  | kg/hectare | | | kg/hectare | | | kg/hectare | | | kg/hectare | | |
| Pre-emergence | 106 | 120 | 190 | 100 | 100 | 120 | 155 | 155 | 180 | 100 | 100 | 100 |
| Post-emergence | 135 | 100 | 100 | 95 | 100 | 100 | 130 | 135 | 200 | 140 | 100 | 100 |

An emulsifiable concentrate was prepared from the test compound D by the method described in Example 1. Thereafter it was diluted with water into spray liquid and used for the treatment of corn and pea. The results are summarized in Table V.

TABLE V

|  | Corn | | | Pea | | |
| --- | --- | --- | --- | --- | --- | --- |
|  | 0.5 | 2 | 5 | 0.5 | 2 | 5 |
|  | kg/hectare | | | kg/hectare | | |
| Pre-emergence | 110 | 115 | 115 | 220 | 180 | 120 |
| Post-emergence | 96 | 103 | 100 | 160 | 155 | 125 |

B. Greenhouse Test

The test was performed in a greenhouse in neutral soil. The seeds were coated with a film containing the test compound. The size of the cultivation pots was 15×30×60 cm. A temperature of 18° to 24° C. in average was maintained. Each test was repeated four times. The average of the results of the repeated tests was related to the average of the untreated controls. Test plant: corn type: SZCS 444. The results are given in Table VI.

TABLE VI

| Test compound | Dosage mg/100 g of seed | Emergence % on the 14th day | Height % on the 31th day |
| --- | --- | --- | --- |
| Control | 0 | 100 | 100 |
| A | 50 | 100 | 110 |
| B | 50 | 106 | 100 |
| C | 10 | 110 | 105 |
|  | 50 | 93 | 115 |
| D | 10 | 106 | 96 |
|  | 50 | 100 | 116 |

C. Greenhouse Test

One proceeds as described at test B., with the difference that instead of using a film coating the active agent is admixed to the soil prior to plant emergence in the form of a 10% microgranulate. Post-emergent treatment is carried out with a spray liquid prepared from an emulsifiable concentrate by the method described in Example 1. Test plant: corn type: KSC 360. A temperature of 24° C. in average is maintained.

The results of the pre-emergent treatments are summarized in Table VII. The height of the plants was determined on the 21th day from the emergence. The results are expressed in the percentage of the control.

TABLE VII

| Test compound | Dosage kg/hectare | Height cm | in percentage of the control |
| --- | --- | --- | --- |
|  | 4 | 60 | 120 |
|  |  | 50 | 100 |
| B | 8 | 55 | 110 |
| C | 2 | 60 | 120 |
| D | 8 | 55 | 110 |
| untreated control | 0 | 50 | 100 |
| acetoneous control | 0 | 50 | 100 |

The results of the post-emergent treatments are summarized in Table VIII. In the time of the treatment the corn was grown to 3 to 5 leaves stage.

TABLE VIII

| Test compound | Dosage kg/hectare | Height cm | in percentage of the control |
| --- | --- | --- | --- |
| B | 2 | 40 | 114 |
| C | 2 | 35 | 100 |
|  | 4 | 45 | 128 |
|  | 8 | 35 | 100 |
| D | 2 | 45 | 128 |
|  | 4 | 35 | 100 |
| untreated control | 0 | 35 | 100 |

The results of the above Tables prove that the compositions containing the compounds of the general formula (I), applied either prior to or after plant emergence, exert a strong stimulating effect on the growth of the plants. Particularly good results were obtained after pre-emergent treatment.

The data relating to the green weights and the dried weights are summarized in Table IX. A post-emergent treatment was applied.

TABLE IX

| Test compound | Dosage kg/hectare | Green weight g | in percentage of the control | Dried weight g | in percentage of the control |
| --- | --- | --- | --- | --- | --- |
| untreated control | 0 | 77 | 100 | 8 | 100 |
| A | 4 | 114 | 147 | 10 | 129 |
|  | 8 | 94 | 120 | 10.5 | 134 |
| B | 2 | 96.5 | 124 | 9.3 | 119 |
|  | 4 | 102 | 131 | 8.7 | 111 |
|  | 8 | 129 | 166 | 10.1 | 129 |
| C | 4 | 122 | 157 | 10.4 | 133 |
|  | 8 | 108 | 139 | 9.1 | 116 |
| D | 2 | 113 | 146 | 6.8 | 87 |
|  | 4 | 145 | 187 | 10.8 | 138 |
|  | 8 | 118 | 151 | 10.6 | 135 |

The data of the above Table show that the compositions according to the invention significantly increase both the green weight and the dried weight of the plants.

The advantage of the plant growth regulating compositions according to the invention lies in the following properties thereof:

strong effect the effect depends on the dosage only in a slight degree the active agents of the general formula (I) are stable compounds slight toxicity on mammals and human.

The invention is illustrated by the following Examples of non-limiting character:

EXAMPLE 1

Preparation of an emulsifiable concentrate (50 EC)

10 parts by weight of (±)-2-(dodecyloxyimino)-1,7,7-trimethyl-bicyclo(2.2.1)heptane are dissolved in 9 parts by weight of xylene, and 1 part by weight of a mixture of an anionic and a non-ionic surfactant e.g. a 2:3 mixture of Atlox 3386 and Atlox 4851 is added to the solution. The mixture is homogenized. An emulsifiable concentrate containing 50% by weight of active agent (50 EC) is obtained, which can be diluted with water to form a spray liquid.

The optically active compounds can be formulated similarly into emulsifiable concentrates.

EXAMPLE 2

Preparation of microgranulates 26 parts by weight of powdered kaoline, 15 parts by weight of potato starch and/or corn starch and 1 part by weight of talc are homogenized with 5 parts by weight of (±)-2-(propyloxyimino)-1,7,7-trimethyl-bicyclo(2.2.1)heptane, and 0.5 parts by weight of Tween 80 polyoxyethylene-sorbitane monooleate are added to the mixture. 2.5 parts by weight of gelatine are swollen in 10 parts by weight of water, then additional 15 parts by weight of water are added, and gelatine is dissolved under heating. The resulting solution is admixed with the above powder mixture. The wet mass is homogenized, granulated on a sieve 14 to 16 mesh, the granulates are dried and then sieved again. A microgranular composition containing 10% by weight of active agent is obtained.

EXAMPLE 3

One proceeds in the way as described in Example 1 or 2, with the difference that another compound of the general formula (I) is used as starting substance.

EXAMPLE 4

Preparation of a seed dressing agent 6 parts by weight of a 10% acetone solution of (±)-2-(propyloxyimino)-1,7,7-trimethyl-bicyclo(2.2.1)heptane are added under stirring to a solution containing 30 parts by weight of acetone, 2.5 parts by weight of hydroxypropyl cellulose, 5 parts by weight of polyethylene glycol (molecular weight: 6000), 20 parts by weight of water and an arbitrary amount of a dyestuff having no germination inhibiting effect.

The optically active compounds can be converted into seed dressing agents by the same method.

EXAMPLE 5

Preparation of sowing-seed foils a. 80 g of a polyvinyl alcohol marketed under the trade name RHODOVIOL 4 (125 P) viscosity of its 4% aqueous solution is 4 cP at 20° C.; hydrolized to 89 mol% are added under stirring to 615 g of 60° C. water. After dissolution 20 g of a polyvinyl alcohol marketed under the trade name of RHODOVIOL 30 (20M) viscosity of its 4% aqueous solution is 30 cP at 20° C.; hydrolized to 98 mol% and 20 g of glycerol are added, and the mixture is stirred vigorously until a homogeneous solution is formed. After 24 hours of standing, whereupon no more bubbles leave, the solution is smeared onto a glass plate in thickness of 0.50 mm by ductor-knife casting, and the deposit is dried at room temperature. The resulting foil, 0.05 to 0.06 mm in thickness, separates from the glass plate to give a tough foil easy to handle. This foil is termed in the following as "control foil".

b. One proceeds as described in point a. above, with the difference that a solution of 0.120 g of (±)-2-(propyloxyimino)-1,7,7-trimethyl-bicyclo(2.2.1)heptane in 5 ml of ethanol is also added to the solution of the polymer before casting. After allowing the bubbles to leave, casting and drying the deposit, a foil, similar to that of point a. but containing 1000 ppm of active agent, is obtained.

c. One proceeds as described in point b. with the difference that a solution of 0.0120 g of (±)-2-(propyloxyimino)-1,7,7-trimethyl-bicyclo(2.2.1)heptane in 5 ml of ethanol is added to the solution to be casted. The resulting foil contains 100 ppm of active agent.

d. One proceeds as described in point b. or c. with the difference that optically active 2-(propyloxyimino)-1,7,7-trimethyl-bicyclo(2.2.1)heptane is applied, instead of the racemic compound.

EXAMPLE 6

Preparation of (±)-2-(allyloxyimino)-1,7,7-trimethyl-bicyclo(2.2.1-)heptane 4.6 g (0.2 moles) of metallic sodium are dissolved in 200 ml of methanol, and 33.4 g (0.2 moles) of (±)-1,7,7-trimethyl-bicyclo(2.2.1)heptane-2-one-oxime are added to the solution. After one hour of boiling 24.0 g (0.2 moles) of allyl bromide are introduced, and the mixture is boiled for 3 hours. The suspension is cooled, the separated sodium bromide is filtered off, the filtrate is concentrated, and the concentrate is subjected to fractional distillation in vacuo.

Yield: 31.2 g (77%) of a colourless oil.

B.p.: 92° C./200 Pa.

$(n)_D^{20} = 1.4882$.

Analysis: calculated: C=75.32%, H=10.21%, N=6.75%. Found: C=75.57%, H=10.20%, N=6.87%.

EXAMPLE 7

Preparation of
(−)-2-(allyloxyimino)-1,7,7-trimethyl-bicyclo(2.2.1-)heptane 4.8 g (0.2 moles) of sodium hydride are added to 150 ml of anhydrous benzene, and a solution of 33.4 g (0.2 moles) of (+)-1,7,7-trimethyl-bicyclo(2.2.1)heptane-2-one-oxime in 50 ml of anhydrous dimethylformamide is introduced into the mixture at 50° C. within 0.5 hours. When gas evolution ceases, the mixture is cooled to 25° C., and 15.3 g (0.2 moles) of allyl chloride are added. The reaction mixture is boiled for additional 2 hours, thereafter shaken with water, the phases are separated, the benzene phase is evaporated, and the residue is subjected to fractional distillation in vacuo.

Yield: 34.4 g (85%)
B.p.: 92°–94° C./200 Pa.
$(n)_D^{20} = 1.4870$.
$(\alpha)_D^{20} = -25.48°$ (c=1, methanol).
Analysis: calculated: C=75.32%, H=10.21%, N=6.75%. Found: C=75.73%, H=10.58%, N=6.96%.

EXAMPLE 8

Preparation of
(±)-2-(propyloxyimino)-1,7,7-trimethyl-bicyclo(2.2.1-)heptane 39.0 g (1.0 mole) of finely powdered sodium amide are added to 800 ml of xylene. The mixture is heated to 50° C., and a solution of 167 g (1.0 mole) of (±)-1,7,7-trimethyl-bicyclo(2.2.1)heptane-2-one-oxime in 200 ml of dimethylformamide is added. When the gas evolution ceases, 123.0 g (1.0 mole) of propyl bromide are added to the mixture at the same temperature, the reaction mixture is allowed to react at 85°–90° C. for 2 hours. Thereafter it is washed several times with water. The active agent content of the xylene solution is determined by gas chromatography.

Yield: 782 g of a xylene solution containing 23.8% of active agent; thus the desired compound is obtained with a yield of 96.0%.

One can also proceed by evaporating the xylene solution in vacuo and purifying the residue by fractional distillation in vacuo.

Yield: 192.6 g (92.0%) of a colourless oil.
B.p.: 90° C. 250 Pa.
(n)=1.4740
Analysis: $C_{13}H_{23}NO$ (209.3): calculated: C=74.59%, H=11.07%, N=6.69%. Found: C=74.70%, H=11.10%, N=6.78%.

EXAMPLE 9

Preparation of
(−)-2-(allyloxyimino)-1,7,7-trimethyl-bicyclo(2.2.1-)heptane 60.0 g (0.55 moles) of allyloxamine hydrochloride are added to a solution of 76 g (0.5 moles) of (+)-1,7,7-trimethyl-bicyclo(2.2.1)heptane-2-one in 225 ml of pyridine and 500 ml of anhydrous ethanol. The reaction mixture is boiled for 3 hours and then it is evaporated in vacuo. The residue is diluted with water, and the aquous mixture is extracted with dichloroethane. The dichloroethane solution is evaporated, and the residue is subjected to fractional distillation in vacuo.

Yield: 85.0 g (81.5%) of a colourless oil.
B.p.: 92°–95° C./200 Pa.
$(n)_D^{20} = 1.4868$.
$(\alpha)_D^{20} = -25.52°$ (c=1, methanol)

EXAMPLE 10

Preparation of
(±)-2-(allyloxyimino)-1,7,7-trimethyl-bicyclo(2.2.1-)heptane

One proceeds as described in Example 8, with the difference that 76.0 g (0.5 moles) of (±)-1,7,7-trimethyl-bicyclo(2.2.1)heptane-2-thione are used as starting substance.

Yield: 83.5 g (80.6%).
B.p.: 94°–96° C./250 Pa.
$(n)_D^{20} = 1.4884$.

EXAMPLE 11

Preparation of
(−)-2-(propyloxyimino)-1,7,7-trimethyl-bicyclo(2.2.1-)heptane 40.0 g (1.0 mole) of finely powdered sodium hydroxide and 50 ml of methanol are added to 800 ml of xylene, and the mixture is boiled for 30 minutes. Then it is cooled to 30° C., 167.0 g (1.0 mole) of (+)-1,7,7-trimethyl-bicyclo(2.2.1)heptane-2-one-oxime are added, and the mixture is heated slowly to boiling. The methanol and the 18.0 ml (1.0 mole) of water formed in the reaction are removed by distillation through a Marcusson trap. Then the reaction mixture is cooled to 30° C., diluted with 200 ml of dimethylformamide, 123.0 g (1.0 mole) of propyl bromide are added, and the mixture is allowed to react at 85°–90° C. for 2 hours. Thereafter it is cooled, washed several times with water, the xylene solution is dried over ignited magnesium sulfate, and its active agent content is determined by gas chromatography. Active agent content is 24.5%.

Yield: 818.5 g (95.8%).

One can also proceed by evaporating the xylene solution in vacuo and purifying the residue by fractional distillation in vacuo.

Yield: 190.9 g (91.2%).
B.p.: 85°–87° C./200 Pa.
$(n)_D^{20} = 22.48°$ (c=2, ethanol).
Analysis: $C_{13}H_{23}NO$ (209.3): calculated: C=74.59%, H=11.07%, N=6.69%. Found: C=74.42%, H=11.15%, N=6.81%.

EXAMPLE 12

Preparation of
(±)-2-(benzyloxyimino)-1,7,7-trimethyl-bicyclo(2.2.1-)heptane

One proceeds as described in Example 10 with the difference that 126.5 g (1.0 mole) of benzyl chloride are used instead of propyl bromide.

Yield: 201.3 (78.2%).
B.p.: 131° C./80 Pa.
$(n)_D^{20} = 1.5250$.
Analysis: $C_{17}H_{23}NO$ (257.4): calculated: C=79.33%, H=9.01%, N=5.44%. Found: C=78.42%, H=8.93%, N=5.36%.

EXAMPLE 13

Preparation of (±)-2-(dodecyloxyimino)-1,7,7-trimethyl-bicyclo(2.2.1-)heptane

One proceeds as described in Example 10, with the difference that 249.2 g (1.0 mole) of dodecyl bromide are used instead of propyl bromide.

Yield: 273.1 g (81.4%).

B.p.: 167° C./40 Pa.

$(n)_D^{20} = 1.4685$.

Analysis: $C_{22}H_{41}NO$ (335.6): calculated: C=78.74%, H=12.32%, N=4.18%. Found: C=78.34%, H=12.53%, N=4.26%.

What we claim is:

1. Racemic or optically active compounds of the formula (I)

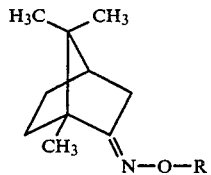

wherein
R represents a $C_{3-12}$ alkyl group optionally substituted by a lower alkoxy group, a $C_{2-4}$ alkenyl group or a phenyl-(lower alkyl) group substituted on the phenyl ring by one or more lower alkoxy groups or halogen atoms.

2. Compounds as set forth in claim 1, wherein R stands for n-propyl, dodecyl or allyl.

3. (±)-2-(dodecyloxyimino)-1,7,7-trimethyl-bicyclo-(2.2.1)heptane,
(±)-2-(n-propyloxyimino)-1,7,7-trimethyl-bicyclo(2.2.1)heptane,
(−)-2-(allyloxyimino)-1,7,7-trimethyl-bicyclo(2.2.1-)heptane,
(±)-2-(allyloxyimino)-1,7,7-trimethyl-bicyclo(2.2.1-)heptane.

* * * * *